US009655562B2

(12) United States Patent
Ellermann et al.

(10) Patent No.: US 9,655,562 B2
(45) Date of Patent: May 23, 2017

(54) SYSTEM AND METHOD FOR PATIENT-SPECIFIC PLANAR VISUALIZATION OF VOLUMETRIC MRI DATA

(71) Applicants: Jutta Ellermann, Minneapolis, MN (US); Patrick Morgan, Minneapolis, MN (US); Mikko Nissi, Minneapolis, MN (US)

(72) Inventors: Jutta Ellermann, Minneapolis, MN (US); Patrick Morgan, Minneapolis, MN (US); Mikko Nissi, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 680 days.

(21) Appl. No.: 14/088,365

(22) Filed: Nov. 23, 2013

(65) Prior Publication Data

US 2014/0187908 A1 Jul. 3, 2014

Related U.S. Application Data

(60) Provisional application No. 61/729,560, filed on Nov. 24, 2012.

(51) Int. Cl.
*A61B 5/055* (2006.01)
*A61B 5/00* (2006.01)

(52) U.S. Cl.
CPC ............ *A61B 5/7235* (2013.01); *A61B 5/055* (2013.01)

(58) Field of Classification Search
CPC ...... A61B 5/055; A61B 5/7235; G01R 33/20; G01R 33/48; G01R 33/5608
See application file for complete search history.

(56) References Cited

PUBLICATIONS

Beck, et al., Hip Morphology Influences the Pattern of Damage to the Acetabular Cartilage, Femoroacetabular Impingement as a Cause of Early Osteoarthritis of the Hip, J. Bone Joint Surg. (Br), 2005, 87-B:1012-1018.
Bittersohl, et al., Feasibility of T2 Mapping for the Evaluation of Hip Joint Cartilage at 1.5T Using a Three-Dimensional (3D), Gradient-Echo (GRE) Sequence: A Prospective Study, Magnetic Resonance in Medicine, 2009, 62 (4):896-901.
Burstein, et al., Measures of Molecular Composition and Structure in Osteoarthritis, Radiol. Clin. N. Am., 2009, 47:675-686.
Ganz, et al., Femoroacetabular Impingement: A Cause for Osteoarthritis of the Hip, Clinical Orthopaedics & Related Research, 2003, 417:112-120.
Ganz, et al., The Etiology of Osteoarthritis of the Hip, an Integrated Mechanical Concept, Clin. Orthop. Relat. Res., 2008, 466:264-272.
(Continued)

*Primary Examiner* — Ruth S Smith
(74) *Attorney, Agent, or Firm* — Quarles & Brady LLP

(57) ABSTRACT

A system and method for providing medical imaging data includes generating T2* maps based on T2* data, registering the T2* maps with 3-D anatomical data reconstructed from the medical imaging data, and segmenting the 3-D anatomical data in a region of interest (ROI). The method also includes generating a 3-D anatomic volume of at least the ROI, flattening the 3-D anatomic volume into a 2-D flattened image, and displaying the registered T2* maps on the 2-D flattened image.

21 Claims, 7 Drawing Sheets

(56) References Cited

PUBLICATIONS

Kohl, et al., Histology of Damaged Acetabular Cartilage in Symptomatic Femoroacetabular Impingement: An Observational Analysis, Hip Int., 2011, 22(2):154-162.
Ito, et al., Femoroacetabular Impingement and the Cam-Effect, J. Bone Joint Surg. (Br), 2001, 83-B:171-176.
Kim, et al., Assessment of Early Osteoarthritis in Hip Dysplasia with Delayed Gadolinium-Enhanced Magnetic Resonance Imaging of Cartilage, Journal of Bone & Joint Surgery, 2003, 85-A(10):1987-1992.
Lattanzi, et al., A New Method to Analyze dGEMRIC Measurements in Femoroacetabular Impingement: Preliminary Validation Against Arthroscopic Findings, Osteoarthritis and Cartilage, 2012, 20:1127-1133.
Leunig, et al., The Concept of Femoroacetabular Impingement, Current Status and Future Perspectives, Clin. Orthop. Relat. Res., 2009, 467:616-622.
Leunig, et al., Evaluation of the Acetabular Labrum by MR Arthrography, J. Bone Joint Surg. (Br), 1997, 79-B:230-234.
Li, et al., Human Hip Joint Cartilage: MRI Quantitative Thickness and Volume Measurements Discriminating Acetabulum and Femoral Head, IEEE Transactions on Biomedical Engineering, 2008, 55(12):2731-2740.
Link, et al., Osteoarthritis: MR Imaging Findings in Different Stages of Disease and Correlation with Clinical Findings, Radiology, 2003, 226:373-381.
Mamisch, et al., MRI of Hip Osteoarthritis and Implications for Surgery, Magnetic Resonance Imaging Clinics of North America, 2010, 18(1):111-120.
Nieminen, et al., T2 Relaxation Reveals Spatial Collagen Architecture in Articular Cartilage: A Comparative Quantitative MRI and Polarized Light Microscopic Study, Magnetic Resonance in Medicine, 2001, 46(3):487-493.
Nieminen, et al., T2 of Articular Cartilage in the Presence of Gd-DTPA2-, Magnetic Resonance in Medicine, 2004, 51(6):1147-1152.
Noguchi, et al., Cartilage and Labrum Degeneration in the Dysplastic Hip Generally Originates in the Anterosuperior Weight-Bearing Area: An Arthroscopic Observation, Journal of Arthroscopic and Related Surgery, 1999, 15(5):496-506.
Palmer, Femoroacetabular Impingement: Caution is Warranted inb Making Imaging-Based Assumptions and Diagnoses, Radiology, 2010, 257:4-7.
Petersilge, Imaging of the Acetabular Labrum, Magnetic Resonance Imaging Clinics of North America, 2005, 13(4):641-652.
Potter, et al., High Resolution Noncontrast MRI of the Hip, Journal of Magnetic Resonance Imaging, 2010, 31(2):268-278.
Regatte, et al., In Vivo Proton MR Three-Dimensional T1p Mapping of Human Articular Cartilage: Initial Experience, Radiology, 2003, 229:269-274.
Sampatchalit, et al., Changes in the Acetabula Fossa of the Hip: MR Arthrographic Findings Correlated With Anatomic and Histologic Analysis Using Cadaveric Specimens, AJR, 2009, 193:W127-W133.
Schmid, et al., Cartilage Lesions in the Hip: Diagnostic Effectiveness of MR Arthrography, Radiology, 2003, 226:382-386.
Watanabe, et al., T2 Mapping of Hip Articular Cartilage in Healthy Volunteers at 3T: A Study of Topographic Variation, Journal of Magnetic Resonance Imaging, 2007, 26(1):165-171.
Welsch, et al., Quantitative T2 Mapping During Follow-Up After Matrix-Associated Autologous Chondrocyte Transplantation (MACT): Full-Thickness and Zonal Evaluation to Visualize the Maturation of Cartilage Repair Tissue, Journal of Orthopaedic Research, 2009, 27(7):957-963.
Ziegert, et al., Comparison of Standard Hip MR Arthrographic Imaging Planes and Sequences for Detection of Arthroscopically Proven Labral Tear, AJR, 2009, 192:1397-1400.
Zilkens, et al., Three-Dimensional Delayed Gadolinium-Enhanced Magnetic Resonance Imaging of Hip Joint Cartilage at 3T: A Prospective Controlled Study, European Journal of Radiology, 2012, 81(11):3420-3425.

SYSTEM AND METHOD FOR PATIENT-SPECIFIC PLANAR VISUALIZATION OF VOLUMETRIC MRI DATA

CROSS REFERENCE

This application is based on, claims priority to, and incorporates herein by reference in its entirety, U.S. Provisional Application Ser. No. 61/729,560, filed Nov. 24, 2012, and entitled, "SYSTEM AND METHOD FOR PATIENT-SPECIFIC MORPHOLOGICAL AND QUANTITATIVE BIOCHEMICAL MRI IMAGES."

STATEMENT REGARDING FEDERALLY SPONSORED RESEARCH

N/A

BACKGROUND OF THE INVENTION

The present invention relates, generally, to systems and methods for magnetic resonance imaging (MRI) and, more particularly, to systems and methods for generating images based on patient-specific morphological data and images.

Femoroacetabular impingement (FAI) is a common cause of intra-articular hip pain resulting in labral tears and associated chondral lesions, which are precursors to hip osteoarthritis (OA). Improved understanding of the condition has led to treatment strategies that seek to both correct these abnormalities and repair the intra-articular damage they have caused. Current trend in orthopedic surgery is focusing on joint preservation instead of joint replacement. Recently many pre-arthritic conditions based on subtle anatomic abnormalities in a young population have been identified. Improved understanding of these conditions has led to treatment strategies that seek to both correct these abnormalities and repair the intra-articular damage they have caused before frank osteoarthritis and therefore irreversible damage will occur. The most important predictor for treatment success is reported to be the integrity of the articular cartilage surfaces. Moderate cartilage damage, unfortunately, can be a challenge to diagnose. Radiographic evaluation using Tönnis grading is the standard of care but has been shown to have poor interobserver reliability. Increasingly, magnetic resonance imaging has been used to investigate these structures for such purposes.

When a substance, such as human tissue, is subjected to a sufficiently-large, uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to another magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation field $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

Although clinical MR imaging has evolved as a reliable tool in depicting labral tears, the adequacy of MRI for cartilage assessment remains poor. Identifying cartilage damage in FAI may be difficult due to the pattern of cartilage damage particular to this condition. In FAI, cartilage damage is frequently limited to the acetabulum and occurs deep within the tissue as a debonding of articular cartilage from bone. This leaves the superficial layer intact, a pattern uniquely ill suited for diagnosis with traditional MRI, which is best at detecting a void at the articular surface. Thus, assessing articular cartilage with MRI requires both high resolution and high contrast-to-noise ratio, especially in the hip. With cartilage quality being the primary prognostic information for any type of joint preservation surgery, and given the difficulty faced today in its imaging and classification, patients inappropriate for joint preservation are not always identified and inappropriate treatments are sometimes recommended.

New MR quantitative cartilage imaging techniques have the potential to be diagnostic and therefore improve treatment decision-making. However, even though arthroscopy is the only practical gold standard (biopsy for histology of patient cartilage is contra-indicated), there are many limitations due to poor spatial correlation of MR findings obtained in slices and the arthroscopy viewed in 3-D.

For example, some have turned to quantitative MR mapping techniques, such as delayed gadolinium-enhanced MRI of cartilage (dGEMRIC). dGEMRIC is the most widely applied investigational technique. It can, however, be time-consuming, logistically difficult to perform, and currently gives a combined value for femoral and acetabular cartilage. As a further limitation of the technique, there is a patient population that cannot be subjected to a dose of gadolinium, such as those with decreased renal function or a history that otherwise implicates the kidney.

Therefore, it would be desirable to have a system and method for visualizing joint and similar structures in a subject as a mechanism to investigate such structures for a variety of purposes.

SUMMARY OF THE INVENTION

The present invention overcomes the aforementioned drawbacks by providing a system and method for acquiring MRI data and generating images of joints and other structures that can be readily correlated with additional data sets. In particular, a system and method is provided to acquire and process data to form a flattened virtual tool applicable for all joints, such as the hip, knee, wrist, shoulder, elbow and ankle, where anatomic landmarks, such as the acetabular notch and acetabular rim, can be precisely correlated between multiple data sets, such as MR images and gold standard arthroscopy.

In accordance with one aspect of the invention, a method is disclosed for evaluating tissue states using a magnetic resonance imaging (MRI) system. The method include acquiring, with an MRI system, T2* data from a portion of a subject including tissue surrounding a joint and generating T2* maps based on the T2* data. The method also includes registering the T2* maps with 3-D anatomical data, segmenting anatomical data in an ROI, and generating a 3-D anatomic volume of at least the ROI. The method further includes flattening the 3-D anatomic volume into a 2-D flattened image and presenting the registered T2* maps on the 2-D flattened image.

In accordance with another aspect of the invention, a magnetic resonance imaging (MRI) system is disclosed. The system includes a magnet system configured to generate a polarizing magnetic field about at least a portion of a subject, a plurality of gradient coils configured to apply a gradient field to the polarizing magnetic field, and a radio frequency (RF) system configured to apply an excitation field to the subject and acquire MR image data therefrom. The system also includes a processor configured to control the plurality of gradient coils and the RF system to acquire medical imaging data including T2* data from a subject, generate T2* maps based on the T2* data, and register the T2* maps with 3-D anatomical data reconstructed from the medical imaging data. The processor is also configured to segment the 3-D anatomical data in a region of interest (ROI), generate a 3-D anatomic volume of at least the ROI, and flatten the 3-D anatomic volume into a 2-D flattened image. The system also includes a display configured to display the registered T2* maps on the 2-D flattened image.

In accordance with yet another aspect of the invention, a method of providing medical imaging data includes acquiring, with an MRI system, medical imaging data including at least T2* data from a subject, generating T2* maps based on the T2* data, and reconstructing 3-D anatomical images of the subject from the medical imaging data. The method also includes registering the T2* maps with the 3-D anatomical images, flattening at least one of the 3-D anatomical images into a 2-D flattened image, and generating the registered T2* maps on the 2-D flattened image. The method further includes calculating a statistical map by applying a given threshold value indicative of a probability of a disease state and displaying at least the registered T2* maps or the statistical map on the 2-D flattened image.

In accordance with another aspect of the invention, a non-transitory computer-readable storage medium is provided having stored thereon instructions that, when executed by a computer processor, causes the computer processor to acquire medical imaging data including T2* data of a subject and generate T2* maps based on the T2* data. The computer processor is also caused to register the T2* maps with 3-D anatomical data reconstructed from the medical imaging data and acquire a 3-D anatomic volume of at least one region of interest (ROI) reconstructed from the 3-D anatomical data. The computer processor is further caused to flatten the 3-D anatomic volume into a 2-D flattened image and display the registered T2* maps on the 2-D flattened image.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 7A shows pattern of acetabular cartilage abnormalities, as evidenced by decreased T2* values corresponding to the red color code on the flattened T2* map. Bandlike extension of markedly decreased T2* values along the chondrolabral junction (PINCER-type), a more diffuse area of abnormality involving the anterosuperior labrum (CAM) indicative of severe cartilage damage. Additional diffuse area of cartilage abnormality more posteriorly, which has been described as 'contrecoup' lesion associated with cam impingement. FIG. 7B shows a left hip acetabulum looking medial: the labrum is separated from the acetabular rim. The lateral acetabular rim is denuded of cartilage leaving a cartilage defect with a thin, fibrous base. FIG. 7C shows a superior femoral head at the head-neck junction: the point of impingement between the femoral neck and acetabular rim is distinguished by an abrupt transition from normal medial femoral head to lateral cartilage destruction.

DETAILED DESCRIPTION OF THE INVENTION

Figure 1:
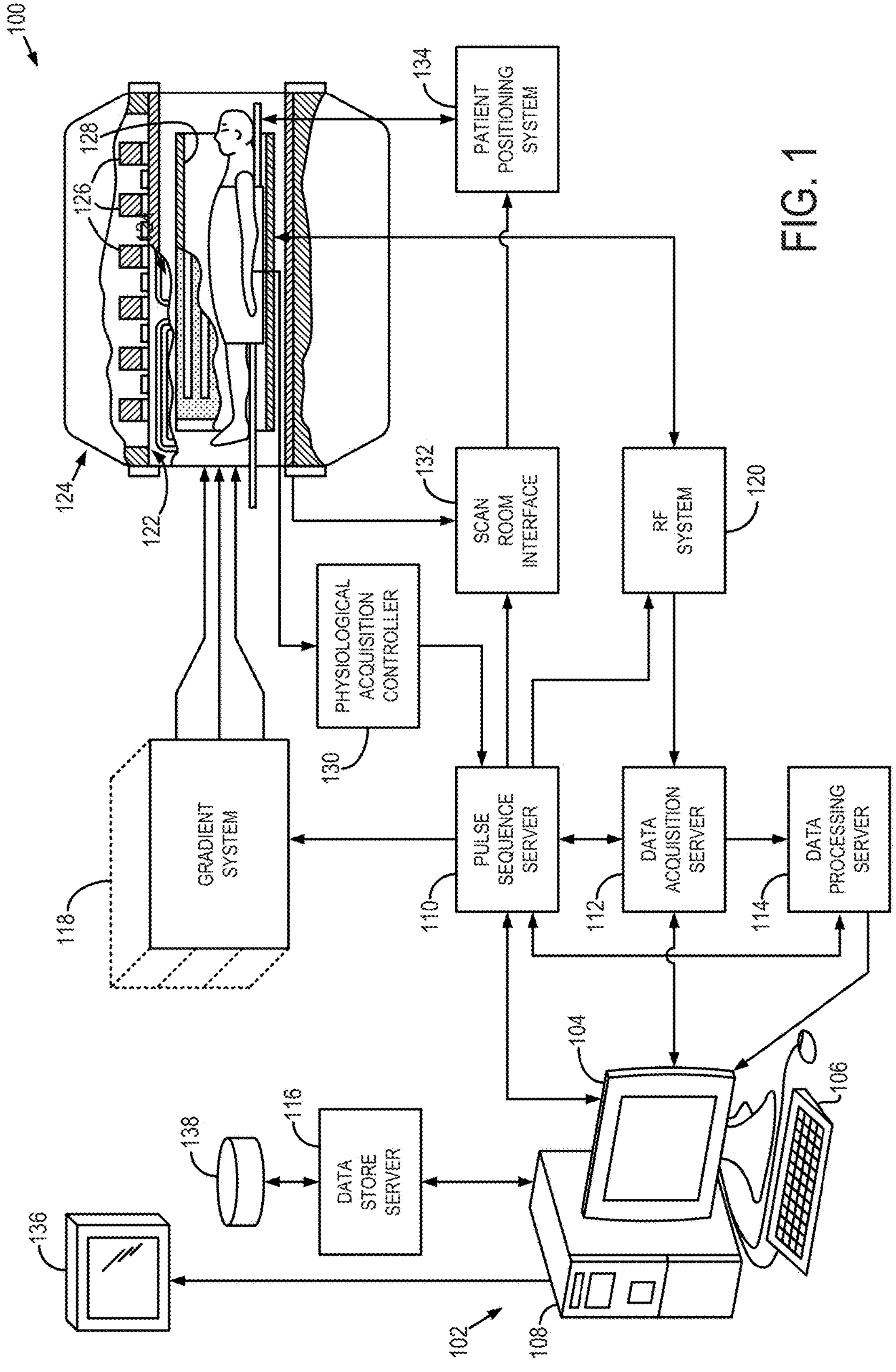
FIG. 1 is a block diagram of an exemplary magnetic resonance imaging (MRI) system that employs the present invention.

Referring now to FIG. 1, an exemplary MRI system 100 for use when practicing embodiments of the provided method is illustrated. The MRI system 100 includes a workstation 102 having a display 104, a keyboard 106, and computer 108. The workstation 102 provides the operator interface that enables scan prescriptions to be entered into the MRI system 100. The workstation 102 may be coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil, such as a body-matrix phased-array coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components $M=\sqrt{I^2+Q^2}$ and the phase of the received MR signal may also be determined $$\varphi = \tan^{-1}\left(\frac{Q}{I}\right).$$

The pulse sequence server 110 also optionally receives patient data from a physiological acquisition controller 130. The controller 130 receives signals from a number of different sensors connected to the patient, such as electrocardiograph (ECG) signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images. Of course, such processing may also be performed on other computer systems that are connected to a network or systems connected to the MRI system 100, such as system 136 described below, or more closely integrated with the MRI system 100.

Images reconstructed by the data processing server 114 are conveyed back to the workstation 102 where they are stored. Real-time images are stored in a data base memory cache (not shown in FIG. 1), from which they may be output to operator display 112 or a display or other connected computer system 136. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

As will be described, the above-described MRI system 100 is capable of a variety of data acquisition and clinical procedures. For example, such system can be used for depicting labral tears and investigating the condition of cartilage or for obtaining other morphological information. As will be described, a system and method is provided that can use quantitative T2* mapping to accurately diagnose damaged acetabular cartilage in FAI. T2* mapping is a widely available clinical sequence with high signal to noise ratio and resolution that does not require intravenous contrast; making it a practical addition to routine clinical scans. The patient-specific acetabular projection presented here allows the clinician to easily assess where on the acetabulum damage has occurred. As a research tool, the combination of T2* data detailing damaged cartilage and a flattened acetabular projection showing the location of the damage will allow a longitudinal study of the natural history of acetabular cartilage in patients with FAI.

Figure 2:
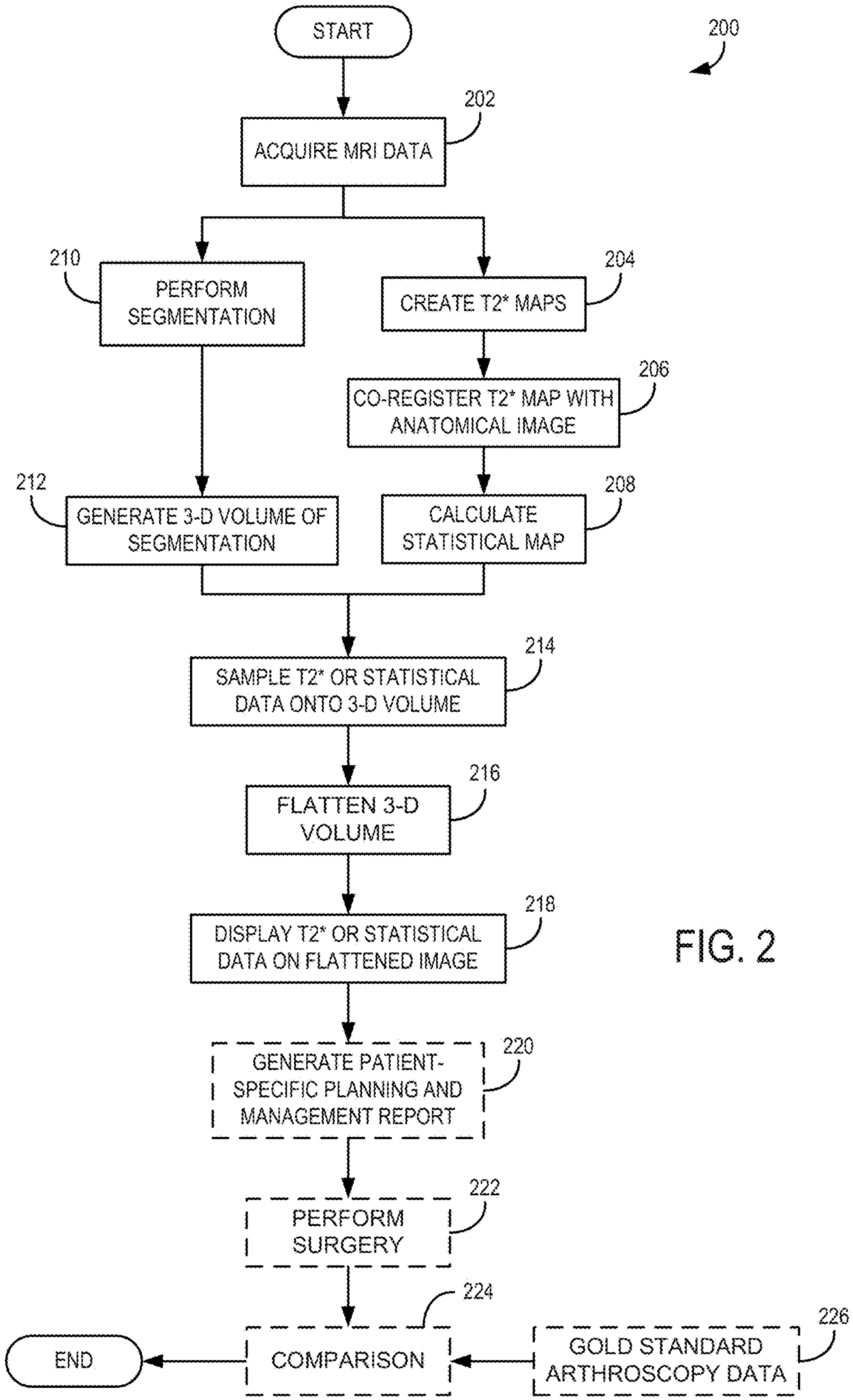
FIG. 2 is a flow chart setting forth steps of an example of a method in accordance with the present invention.
Figure 3:
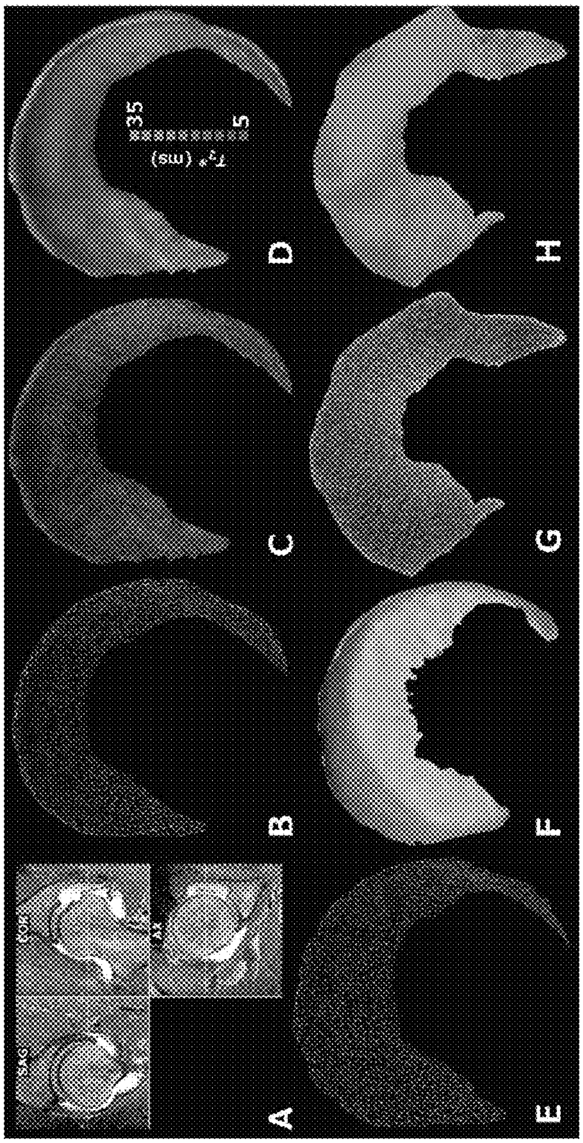
FIGS. 3A-H are examples of images created when applying a The flattening process in accordance with the present invention to 3-D MR datasets acquired in accordance with the present invention.

In particular, referring to FIG. 2, an example of a process 200 in accordance with the present invention begins with the acquisition of MRI data at process block 202. In particular, a clinical MRI hip imaging protocol may be performed using proton density, T1- and T2-weighted turbo spin echo (TSE) imaging acquisitions.

T2 relaxation time has been used as an indirect indicator of structural changes within articular cartilage due to its sensitivity to alterations in water content, interaction between water molecules, and spatial collagen architecture. T2 mapping is mainly acquired with spin-echo techniques and requires relatively long acquisition times. T2* relaxation is a combination of inherent "true" T2 relaxation and additional T2' relaxation due to both microscopic and macroscopic magnetic field inhomogeneities (1/T2*=1/T2+1/T2'). The reversible relaxation due to these inhomogeneities can be refocused and thus removed using a 180 degree pulse for measurement of T2. T2* maps can be acquired relatively quickly with gradient-echo (GRE) sequences and have shown comparable results in cartilage imaging. In GRE sequences, there is no refocusing pulse, and the additional relaxation effects characterized with the parameter T2' are not removed. Although both T2 and T2* indirectly reflect water content and collagen fiber orientation within articular cartilage, the T2* technique is more sensitive to changes in magnetic susceptibility over tissue interfaces, such as the change from cartilage to bone at the osteochondral junction. Thus, T2* is sensitive to T2 changes as well as to additional mechanisms that contribute to T2'. While the latter component is affected by bulk inhomogeneities in the static magnetic field, which are typically not of interest, it is also affected by the differences in tissue composition at a microscopic level, such as changes at the osteochondral interface and the susceptibility changes induced by para- and/or diamagnetic alterations within the cartilage matrix.

MR arthrography and histological correlations in cadaveric specimens have revealed fibrocartilage transformation with superimposed deposition of calcium hydroxyapatite. Furthermore, fibrocartilagenous metaplasia undergoes mineralization by osteoblasts with penetration of capillaries at the osteochondral junction and subsequent deposition of osteoid matrix. This was also confirmed in small biopsies of symptomatic patients with femoroacetabular impingement, indicating the correlation of cartilage delamination in FAI with loss of normal hyaline cartilage architecture, which had been transformed into fibrous connective tissue. Granulation tissue with calcifications and osseous callus at its base was noted in reparative zones. The deposition of osteoid matrix is often perceived as subtle punctate calcific densities within the labrum and the femoroacetabular joint space on plain radiographs.

Given these histological findings, the present invention recognizes that such microscopic inhomogeneities inherent to the disease process can increase the sensitivity of T2* relative to T2. The damaged acetabular cartilage consists mostly of fibrous metaplasia and fibrocartilage-like tissue lacking a highly organized collagen network, which is reflected by the loss of the zonal variation of T2 observed in native cartilage. These histological changes, shown to take place with repetitive microtrauma, suggest that the T2* values are likely to be sensitive to changes due to FAI. The results clearly indicate that in areas of cartilage lesions or delamination. T2* values are markedly decreased. Similar to previous accounts, microfracture repair sites with fibrocartilage-like repair tissue show lower mean T2-values than control cartilage after microfracture procedures. A lower T2-value may suggest overall loss of mobile water molecules and decreased mobility of the remaining water molecules within the milieu of randomly oriented fibrous tissue. The additional T2* effect due to the lack of a 180 degree refocusing pulse, which would be applied in pure T2-mapping, can arise from the calcium deposits, further decreasing the measured T2* relaxation time.

With this in mind, imaging parameters for T1-weighted TSE images in three oblique orthogonal planes may include: TE=10 ms, TR=568-787 ms, and slice thickness 3-4 mm, with in plane resolution of about 0.8×0.6 $mm^2$. Subsequently T2*-weighted images may be collected in 7 oblique sagittal slices with an in-plane resolution of 0.5×0.5 $mm^2$, 3 mm slice thickness and TE=4.2, 11.3, 18.4, 25.6 and 32.7 ms, respectively, with TR=1040 ms, and field of view 18×18 cm.

Referring again to FIG. 2, following the acquisition of the T2* data, at process block 202. T2* maps may be calculated inline in process block 204, for example, based on calculations of the monoexponential decay. Usable parametric data for subsequent processing can be either in 2-D or 3-D format.

It should be also noted that the absolute T2* relaxation time values are affected by a number of factors, such as acquisition parameters, regional variations in the transmit RF (B1) field, eddy currents, as well as the chosen fitting algorithm and fitting parameters. Due to this, caution should be exercised interpreting and extrapolating the disease probability threshold T2* value to other sites and data acquired on scanners from other manufacturers.

In developing the present invention, T2* studies were conducted as an add-on to the regular clinical scan with intra-articular Gadolinium; as such Gadolinium was present during the T2* mapping. Others have reported that the influence of Gadolinium on cartilage T2 is insignificant concluding that in clinical trials involving Gadolinium (dGEMRIC), T2 measurement could be done during the same scanning session, unless very high doses are utilized. The studies yielded experimental T2* evidence consistent with this. The T2* relaxation times of the weight bearing acetabular cartilage of two patients were assessed with T2* maps, measured both with and without Gadolinium during the same scan. The comparison between the datasets demonstrated near-perfect agreement with an $R^2$ value of 0.97 between the pre- and post-Gadolinium T2* values, indicating that 97 percent of the variation in pre-Gadolinium T2* is explained by the post-Gadolinium T2*. The average difference in the relaxation times was less than 1 ms (pre-Gd T2*=19.6 ms, post-Gd T2*=20.3 ms, n=129, p=0.1145, Wilcoxon-test), further indicating that with the current (typical clinical scan) protocol, the influence of Gadolinium on T2* relaxation time of acetabular cartilage is virtually non-existent.

The studies also found that T2* mapping, with its inherent high signal-to-noise ratio (SNR) and resolution, allows for the division of hip cartilage into femoral and acetabular cartilage. This is a significant advantage when imaging patients with FAI, a condition in which isolated acetabular cartilage damage is common. We further divided the acetabular ROIs into deep and superficial halves; our finding of significantly different T2* values in the deep and superficial layers is in keeping with previous reports.

The calculated T2* maps can be co-registered with the anatomical data. Co-registration in process block 206 may be done for example using the T2* data that was acquired in process block 202 for creation of the T2* maps in process block 204.

Based on a given threshold value, which may be determined in a patient population using the invention and comparison with arthroscopy gold standard, a statistical map can be calculated in process block 208. The statistical map may anatomically correspond with the co-registered T2* map. For example, a threshold value of 28 ms may be used to create such statistical map that will indicate probability of diseased cartilage.

Parallel therewith, patient-specific anatomical image segmentation can be performed at process block 210. In this example, the segmentation may be to segment acetabular cartilage in the anatomical 3-D-SPACE or 3-D DESS data-set. This may be achieved, for example, using "Osirix" or "BrainVoyager" software. The image segmentation can be used, at process block 212, to generate a 3-D volume of the segmentation. For example, a patient-specific anatomical 3-D cartilage volume, which may be in grayscale, may be created in process block 212.

At process block 214, the T2* maps created at process block 204 and co-registered with the anatomical data in process block 206 or statistical maps created at process block 208 can be sampled onto the segmented 3-D anatomical volume, for example, using "Matlab" and "BrainVoyager" software. As such a patient specific 3-D parametric map superimposed on the respective cartilage anatomy is created. Subsequently, at process block 216, the anatomical 3-D volume can be flattened onto 2-D plane to generate patient-specific anatomical flattened virtual tool, using which, quantitative parametric 3-D MRI data may be represented in a 2-D view. For example, the flattening may be achieved using "BrainVoyager" software and the Cartilage flattening-plug-in, developed by Rainer Goebel from the University of Maastricht, The Netherlands, and available at brainvoyager.com. At process block 218, the merged, segmented T2* maps or statistical images can be displayed.

For example, the above-described process allows for personalized, patient-specific pre-surgical planning and may aid in patient management decision at optional process block 220. The clinical imaging results in concert with the flattened 2-D quantitative parametric images may indicate reliably if surgery is advised at optional process block 222. If surgery is decided, the 2-D maps assessed at process block 218 enable ready comparison at optional process block 224 against gold standard arthroscopy information 226 to allow improved clinical analysis.

For example, using the above-described process, analysis shows that there was visual correlation between hip arthroscopy and the flattened T2* map of the acetabulum in the qualitative amount of cartilage damage and its location. The flattened 2-D image of the quantitative 3-D T2* acetabular cartilage map accurately depicted the pattern and degree of cartilage damage found during hip arthroscopy. Likewise, markedly decreased T2* relaxation time values were found in regions of articular cartilage identified as abnormal intraoperatively. The results demonstrate that with T2* relaxation time mapping and 2-D flattening, MR imaging is capable of assessing the quality of articular cartilage in femoroacetabular impingement at a level comparable to the gold standard of diagnostic hip arthroscopy.

So, the result of the above-described process is to provide patient-specific morphological and parametric MRI data, now represented as flattened virtual tool that allows for pre-operative planning, including the ability to perform direct assessment and comparison with gold standard arthroscopy. In the above example of an orthopedic application, the orthopedic surgeon may add his intraoperative findings onto this patient specific 2-D representation of the anatomy and quantitative MRI properties to allow for documentation and validation. This can be done by grading of cartilage integrity, as seen in arthroscopy, based on the pre-existing Beck scale of cartilage classification for the hip.

However, it is important to correlate the data for ready comparison. For example, the use of a clock face nomenclature to describe acetabular findings is common to both the radiology and orthopaedic literature. It is important to note that these two uses are anatomically unrelated and cannot be directly compared. In the radiology literature, 12:00 o'clock is defined by the MR image and is the superior point on a sagittal slice, which depends on the patient's lumbar lordosis and/or pelvic tilt. In the orthopaedic literature, however, 12:00 o'clock is defined by anatomic landmarks and is the point on the acetabular rim directly above and centered on the acetabular notch. However, the acetabular projection technique presented here allows for an accurate comparison of imaging and surgical findings.

The present method developing the "virtual acetabulum" has been demonstrated in a group of patients with an early pre-arthritic hip condition. Before the present invention, there was no such MR data processing tool available to provide the orthopedic surgeon with the most relevant qualitative and quantitative 3-D data in 2-D representation that is comparable to the view of the arthroscopy. By using the T2* mapping technique, along with the clinical follow up data, a clinician can identify patients that will benefit from arthroscopic surgery to repair both labrum and cartilage, and which of those will not.

Example I

A 3T clinical imaging protocol (Trio; Siemens Medical Solutions, Erlangen, Germany), with a body-matrix phased-array con, was used. This protocol is detailed in the following table:

| Sequence | Plane | TR/TE (ms) | Slices and thickness | Resolution (mm) | Scan time |
|---|---|---|---|---|---|
| T1w TSE FS | AX, SAG, COR | 540-780/10-12 | 24, 3-4 mm | 0.45 × 0.6 | 3-4 min |
| T2w TSE FS | COR, SAG, | 2200-2600/ 68-75 | 24, 3-4 mm | 0.45 × 0.6 | 3-4 min |
| PDw TSE | COR, Obl. AX | 2000-2200/ 27-39 | 24, 3-4 mm | 0.45 × 0.6 | 3-4 min |
| SPACE | 3-D | 1000/30 | — | 0.75 × 0.75 × 0.75 | 5:17 min |
| DESS | 3-D | 12/4.9 | — | 0.75 × 0.75 × 0.75 or 1 × 1 × 1 | 5:50 min |

-continued

| Sequence | Plane | TR/TE (ms) | Slices and thickness | Resolution (mm) | Scan time |
|---|---|---|---|---|---|
| T2* GRE FS | SAG | 1040/4.2, 11.3, 18.4, 25.6, 32.7 | 24, 3 mm | 0.52 × 0.52 interpolated to 0.26 × 0.26 | 7 min |

In the table,
FS = fat saturated,
AX = axial,
SAG = sagittal,
COR = coronal,
Obl. = oblique,
ms = milliseconds.

The protocol required approximately forty-five minutes to complete with the T2* data obtained during the final 7 minutes to prevent time dependence of T2* values after unloading T2* maps were generated inline using the "Mapit" software package (Siemens Medical Solutions).

Post-processing was performed independently by the primary reviewer (C.Z., second year orthopaedic resident) who was blinded to the patients' clinical information. Acetabular orientation was standardized on sagittal images by using a line passing through the center of the femoral head, perpendicular to the transverse acetabular ligament (TAL) defining the 12:00 o'clock position superiorly and the 3:00 o'clock anteriorly. The border between the acetabular and femoral articular cartilage layers was defined as the low intensity line seen on the second echo of the gradient recalled echo sequence (TE=11.2 s). Cartilage damage ROIs were defined in the anterior-superior acetabulum because this area has the highest reported incidence of damage in patients with FAI. Acetabular cartilage in this region as seen on three consecutive sagittal slices was divided into five ROIs in each slice between 12 o'clock and the chondrolabral junction using the image processing application OsiriX™ software (OsiriX™ v.4.1.1, 32-bit, osirix-viewer.com. OsiriX™ is a trademark owned by Pixmeo Sàri Société à responsabilité limitée of Switzerland.), for a total of fifteen anterior-superior ROIs. For assessment of differences between deep and superficial tissue layers, each ROI was further split (50/50) depth-wise. Each layer plus the full thickness acetabular cartilage was subsequently assessed. Four ROIs were defined in the posterior-medial acetabulum, where articular cartilage damage is infrequent in FAI, to serve as control ROIs. These were processed in an identical fashion. Note that this landmark-based definition resulted in ROIs comparable between the patients even though the volume (and number of voxels) varied from patient to patient depending on their physical size. To enable comparison with surgical assessment, imaging data was anatomically located to its position on the patients' acetabulum with the use of a patient-specific, flattened acetabular projection. Flattened projections were created by first segmenting the acetabular cartilage using either the 3-D DESS or SPACE data, depending on which was available in the clinical protocol. A 3-D volume mesh was then generated from the segmentation data using BrainVoyager software (BrainVoyager QX 2.4, brainvoyager-.com). T2* maps were co-registered with the anatomical data and then sampled on the surface of this 3-D mesh using BrainVoyager software and Matlab software (Matlab 2011b, The MathWorks, Natick, Mass., USA) to generate surface maps representing the T2* data of the acetabular cartilage. Finally, the 3-D mesh of the acetabular cartilage was flattened on a 2-D plane using BrainVoyager software and the T2* surface map was then applied on the flattened mesh allowing the entire anatomically located set of T2* acetabular data to be seen on a single image, as shown in FIG. 3A-3H.

In particular, acetabular cartilage is segmented on a SPACE or a DESS 3-D dataset as exemplified in FIG. 3A. In FIG. 3B, a 3-D mesh is generated from the segmentation. The T2* data is sampled from the co-registered T2* dataset on the surface of the mesh, as illustrated in FIGS. 3C and 3D. For flattening, the articular surface of the segmentation is separated from the bone-side surface, as shown in FIG. 3E. The mesh is flattened on to a plane, as illustrated as an intermediate step in FIG. 3F and shown with filled mesh and fully flattened mesh in FIG. 3G. Finally, the T2* data shown in FIG. 3D is displayed on the flat mesh in FIG. 3H.

All arthroscopies were performed by the same orthopaedic surgeon (P.M., 7 years of experience). A patient-individualized, flattened anatomic map of the acetabulum was presented to the orthopedic surgeon, on which simple, obvious bony landmarks could be co-located at the time of surgery. The psoas sulcus; the highest point of the acetabular notch along with the parallel medial and lateral borders of the acetabular notch; and the base of the anterior lunate cartilage are readily used to define the midpoint, top, and bottom of the anterior lunate cartilage, respectively. The medial borders of the notch define the lunate's anterior-medial borders. The posterior lunate has a consistent sulcus similar to the anterior psoas sulcus and the superior point of the notch. Individual ROIs once located in space were measured relative to a flexible probe of 2 mm in diameter, which served as a ruler. As each patient had individualized ROIs (blinded to the T2* values) known to the surgeon, the correlation between the patient—individualized anatomic maps and the arthroscopic findings were accomplished by 1) locating the ROI by triangulating between these readily identifiable bony landmarks and then refining the location with a ruler.

Operative findings were recorded on the patient-specific acetabular projection. A modified Beck scale was utilized to characterize the degree of articular cartilage damage, as provided below in table 2.

| Score | Notation | Description |
|---|---|---|
| 1 | Normal | Macroscopically sound cartilage |
| 2 | Early changes | Softening, fibrillation, cartilage remains adherent to underlying bone |
| 3 | Debonding | Loss of fixation to the subchondral bone, carpet phenomenon |
| 4 | Cleavage | Loss of fixation to the subchondral bone; frayed edges; thinning of the cartilage; flap |

-continued

| Score | Notation | Description |
|---|---|---|
| 5 | Defect, fibrous base | Full thickness loss of articular cartilage with a thin fibrous-tissue covered base |
| 6 | Defect, eburnated base | Full thickness cartilage loss with a base of eburnated bone |

Control ROIs were specifically assessed for clinical signs of cartilage damage. The surgeon of record performed all assessments and while provided with the clinical radiology report, was blinded to the T2* mapping data.

ROIs were assigned to four groups based on the Beck scale: 1, 2, 3+4 and 5+6 (Table 2). Subsequently, the T2* values were compared among these groups by conducting pair-wise Wilcoxon rank-sum tests at significance level 0.05. To ensure a family-wise error rate no larger than the significance level, we corrected the p values using Holm's method. Finally, the groups were investigated with multiple dichotomizations to estimate a predictive model using each of the resulting binary datasets. We then used receiver operating characteristic (ROC) analyses to evaluate the sensitivity and specificity of our predictive models and to define a threshold T2* value for damaged articular cartilage. The threshold value was taken to be the value of T2* that corresponds to the point on the ROC curve at which the sensitivity is equal to 1−specificity.

Interobserver reliability was assessed by assigning two examiners of differing experience levels (C.Z. and M.B., 1 year of experience) to independently generate ROIs and T2* values from 5 randomly selected hips. Each examiner made measurements from the same sagittal slices of blinded MR images. Subsequently, a single-measure interclass correlation coefficient (ICC) was used to determine within-ROI variability between groups.

Assessment of the variation in the T2* data due to the orientation with respect to the main magnetic field (B0), magic angle effect, was done by fitting a linear regression model with T2* values as the response and $3^2\{(-15)/180\}-1$ as the predictor, where x is the angle in degrees. A fixed angle of 15 degrees was used to correct for the average orientation of the 12 o'clock line that was used in the calculation of the ROI angles.

All statistical analyses were performed by a biostatistician using version 2.15.2 of the R software package (R core Team 2012. R: A language and environment for statistical computing. R Foundation for Statistical Computing, Vienna, Austria).

Figure 4:
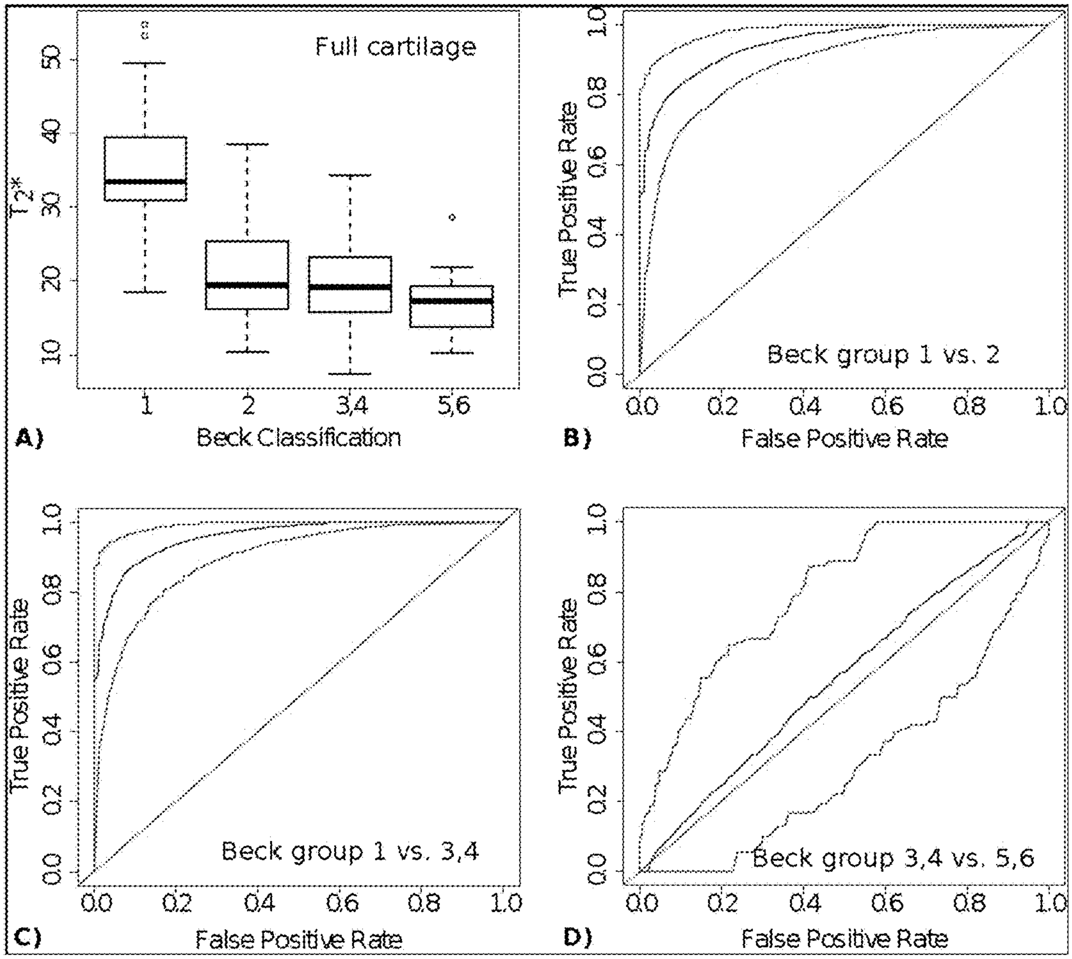
FIG. 4A is a graph showing box plots for T2* values in the four groups of a modified Beck scale: 1, 2, 3+4 and 5+6 over all the patients in the pathology ROIs.
FIG. 4B is a graph showing a receiver operating characteristic (ROC) curve and delineation of a 95 percent confidence band of the ROC curve for the differentiation between Beck groups 1 and 2 using T2*.
FIG. 4C is a graph showing a ROC curve for differentiation between groups 1 and 3+4, with group 1 being clearly differentiated from the more diseased cartilage.
FIG. 4D is a graph showing a lack of differentiation between groups 3+4 vs. 5+6.

Twenty-eight consecutive hip MRIs from twenty-six patients were identified that matched the inclusion criteria. Eighteen patients were female and eight were male. Mean age all (28 hips): 28.2; 12-53 years, male (9 hips): 26.7; 16-53 years, female (19 hips): 28.9; 12-46 years. Patients presented with characteristic symptoms of FAI including groin pain, sitting intolerance, and limited hip range of motion. An average of 3 months elapsed between the time of MR imaging and arthroscopy. Radiographic evaluation revealed an average alpha angle of 62.6+/−14.5 degrees and an average lateral center edge angle of 28.9+/−6 degrees (FIG. 4). Tönnis grading revealed nine hips with Tönnis 0 and 19 patients with Tönnis 1 joint space.

Fifty-seven ROIs were studied per patient for a total of 532 full-thickness ROIs, further split into superficial and deep halves, resulting in 1596 ROIs overall. The results of the quantitative T2* relaxation time mapping for the deep, superficial, and full thickness acetabular cartilage layers are summarized below in table 3:

| | Beck = 1 | Beck = 2 | Beck = 3, 4 | Beck = 5, 6 |
|---|---|---|---|---|
| Full cartilage thickness | 35.3 ± 7.0 ms | 20.7 ± 6.0 ms | 19.8 ± 5.6 ms | 16.8 ± 4.0 ms |
| Superficial cartilage | 40.1 ± 10.3 ms | 24.2 ± 7.4 ms | 22.5 ± 6.8 ms | 17.7 ± 5.0 ms |
| Deep cartilage | 30.6 ± 6.5 ms | 17.4 ± 5.5 ms | 17.2 ± 5.1 ms | 15.8 ± 4.0 ms |

Thirty-two percent of the arthroscopic ROIs were classified as Beck 1 (172 of the 532 full-thickness ROIs), with normal, macroscopically sound articular cartilage. Thirty percent of the ROIs were classified as Beck 2 (160 of 532), showing cartilage changes of softening and fibrillation. Thirty-two percent (171 of 532) were found to have either cartilage debonding or gross delamination consistent with cleavage with 21 percent (112 of 532) classified as Beck's scale 3 and 11 percent (59 of 532) Beck's scale 4 changes. Approximately 4 percent (21 of 532) of ROIs had a fibrinous base (Beck 5) and only 2 percent (8 of 532) an eburnated base (Beck 6) denuded of cartilage. In 95 percent (503 of 532) of the ROI's (Beck 1-4) the cartilage thickness was preserved. Due to the exclusion of patients with joint space narrowing (Tönnis grade 2 and higher), only a very limited number of ROIs (5 percent, 29 of 532) exhibited altered thickness of cartilage. The area of acetabular cartilage delamination as depicted on arthroscopy correlated with markedly decreased T2* values on the quantitative MRI map, whereas the plain radiograph revealed Tönnis grade 0-1 with a preserved joint space.

Interobserver reliability for the generation of acetabular deep, superficial and full thickness ROIs was found to have an estimated intraclass correlation coefficient (ICC) of 0.88 with a 95 percent confidence interval of (0.82, 0.92). Assessment of the magic angle effect in the articular cartilage showed that at most 2 percent of the variation in the T2* data were due to orientation with respect to the main magnetic field (B0) as indicated by $R^2=0.02$ of the linear regression model.

T2* maps were found to have significantly lower values in regions with surgically identified cartilage damage (mean 20.7±6.0 ms) than for normal cartilage (mean=35.3±7.0) in patients with femoroacetabular impingement ($p<0.001$) (Table 3). In the superficial layer the T2* values were consistently higher than in the deep cartilage layer ($p<0.001$). For full, superficial, and deep cartilage there was a significant difference between Beck scale 1 and 2, as well as between Beck scale 1 and 3.4 (both with p=<0.001). The respective box plots for T2* values in the different Beck scale groups are demonstrated in FIG. 4A. The ROC curves indicated clear differentiation for all dichotomizations separating group 1 (normal) from all other Beck Scale levels, as shown in FIGS. 4B and 4C. For ROC analyses of higher grades (i.e. 3.4 vs. 5.6), no clear differentiation was observed, as shown in FIG. 4D. ROC curve analysis showed that a 91 percent true positive and 13 percent false positive rate corresponded with a threshold T2* value of 28 ms for defining cartilage damage, a value that corresponds to an estimated probability of disease of 0.8. Note that all p-values were corrected for multiple comparisons. The unadjusted p-values were so small that adjusting for multiple comparisons did not affect the conclusions.

The above results stand in stark contrast with prior efforts. For example, since its description and means of surgical correction were first published, operative management of femoroacetabular impingement has become increasingly common. However, significant variation has been seen in surgical outcomes, which is an issue that has been explained in part by the presence or absence of articular cartilage damage. Due to the abnormal contact stresses between the reduced femoral head/neck offset and the acetabulum, debonding occurs between the cartilage and subchondral bone plate. This "inside out" process of articular cartilage delamination progressing from deep to superficial is unique to FAI. Therefore, previous imaging and arthroscopic staging, such as the ICRS classification that were created to describe the degenerative changes in the knee from superficial to deep, are limited in their application for the hip.

Currently, radiographic Tönnis grading is the most commonly employed means of screening for level of cartilage damage incompatible with joint preservation surgery. Tönnis grading, unfortunately, is unreliable. As detailed in the provided example, the study provided findings consistent with this; despite restricting surgery to patients with Tönnis grades 0 or 1, 68 percent (360 out of 532) of the ROIs analyzed showed evidence of cartilage damage upon arthroscopy underscoring the relative insensitivity of radiographs in determining the extent of osteoarthritis in this cohort.

Efforts to improve cartilage assessment with routine MR have been disappointing. Cartilage debonding and gross delamination may appear normal on routine MR and MR arthrogram. The "inverted Oreo cookie sign", seen when contrast material becomes interposed between debonded cartilage and bone, is specific but has low sensitivity. We question if this is a consequence of the hip's inherent congruency, which may prevent contrast flow between delaminated cartilage and bone. The occurrence of a linear, dark line on T1-weighted images extending from the chondrolabral junction has also been noted. This line is of uncertain significance and may simply represent a truncation artifact. Low T1- and T2-weighted signal intensity has been observed in delaminated cartilage. Without the ability to be quantified this observation has been of limited utility.

In this study, however, we report new MR imaging findings, confirmed by arthroscopy that may have significant clinical diagnostic implications. Namely, we found a significant correlation between cartilage damage and decreased T2* values. This is consistent with previous reports. ROC curve analysis showed that a 91 percent true positive and 13 percent false positive rate corresponded with a threshold T2* value of 28 ms at 3 Tesla for defining cartilage damage, a value that corresponds to an estimated probability of disease of 0.8. We believe that this threshold will be helpful for clinicians interpreting the results of T2* maps and may provide the basis for an MR-guided cartilage screening tool similar to, but more reliable than Tönnis grading.

Example II

A 34-your old male with multiple years of history of severe bilateral groin pain was evaluated after failing to improve with comprehensive non-operative management including activity modification, oral pain medications, physical therapy, injections, and spinal procedures. The patient described his symptoms as sharp, aching, and worsened by hip flexion activities. Physical examination of the hip revealed a positive anterior impingement test, which reproduced his symptoms and marked lack of flexion and internal rotation.

Figure 7:
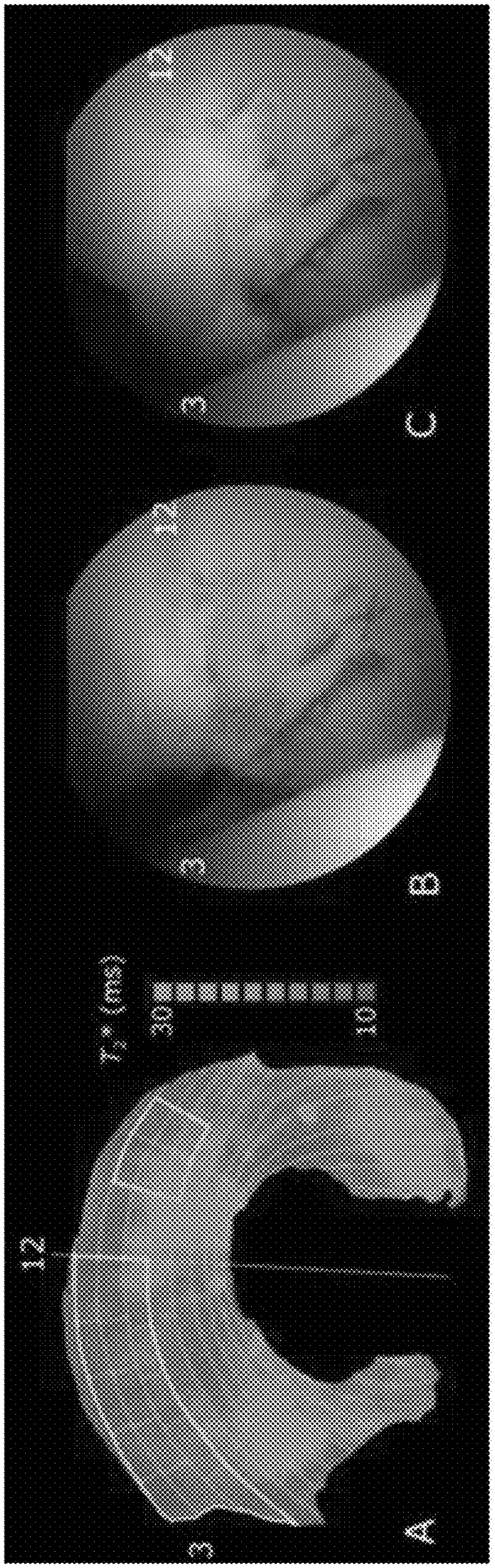
FIG. 7 is a flattened acetabular cartilage T2* map (A) aligned with intraoperative findings (B, C). Using the clock face as a reference frame, 12 o'clock is assumed to be superior and 3 o'clock anterior. Specifically.

An MR arthrogram was performed using a 3T system (Trio; Siemens Medical Solutions, Erlangen, Germany) with a body-matrix phased-array coil. Following the intra-articular administration of Gadolinium, a standard clinical imaging protocol was performed, using PD, T1- and T2-weighted turbo spin echo (TSE) sequences. A 3-D-SPACE sequence was acquired for 3-D cartilage segmentation and radial reconstruction. Subsequently, T2*-weighted images were collected in 24 sagittal oblique slices with an in-plane resolution of 0.5×0.5 mm2, 3 mm slice thickness and TE=4.2, 11.3, 18.4, 25.6 and 32.7 ms, TR=1040 ms and field of view of 18×18 cm. A previous report indicated that T2 relaxation time of cartilage in the presence of Gadolinium contrast agent does not significantly deviate from T2 without the contrast agent. The T2* maps were calculated inline using the Siemens Mapit software. Regions of interest (ROI) were defined for 5 acetabular cartilage zones within each of 3 sagittal slices nearest in the anterosuperior acetabulum using OsiriX software (OsiriX 4.1.1), ROIs are depicted in FIG. 7A. Furthermore, the acetabular cartilage was segmented in the 3-D-SPACE dataset. Finally the T2* maps were sampled on the segmented 3-D acetabular cartilage volume and subsequently flattened using BrainVoyager software (BrainVoyager 2.4) and 'Cartilage flattening'-plugin to allow for comparison with the intraoperative recording of the Orthopedic surgeon.

After failing comprehensive medical treatment, the patient chose to proceed with an arthroscopic cam anatomy correction and labral repair. The patient was positioned and then prepped and draped in a normal standard fashion as described by Byrd and an image intensifier was utilized to establish access to the joint. A modified Beck scale was used for the intraoperative cartilage assessment; grade 1=normal: macroscopically sound cartilage, grade 2=early changes: softening, fibrillation, remains adherent to underlying bone, grade 3=debonding: loss of fixation to the subchondral bone, carpet phenomenon, grade 4=cleavage: loss of fixation to the subchondral bone; frayed edges; thinning of the cartilage; flap, grade 5=defect with fibrous base: full thickness loss of articular cartilage with a thin fibrous-tissue covered base, grade 6=defect with eburnated base: full thickness cartilage loss with a base of eburnated bone. Surgical intervention included a labral repair with suture anchors to address the labral pathology and a microfracture of the acetabulum. Cam lesion resection was performed arthroscopically using fluoroscopy, dynamic examination, and the location of a clear impingement trough as guides.

Post-operatively, the patient was admitted overnight for observation and pain control. Outpatient physical therapy for passive range of motion was initiated on post-operative day two. Weight bearing was limited for six weeks to allow for maturation at the microfracture site. He was seen at 3 and 6 weeks for wound and rehabilitation checks and at 3, 6, and 12 months for clinical follow-up at which time his groin symptoms had improved to the point that he no longer required pain medication and was able to partake in fitness activity.

Figure 5:
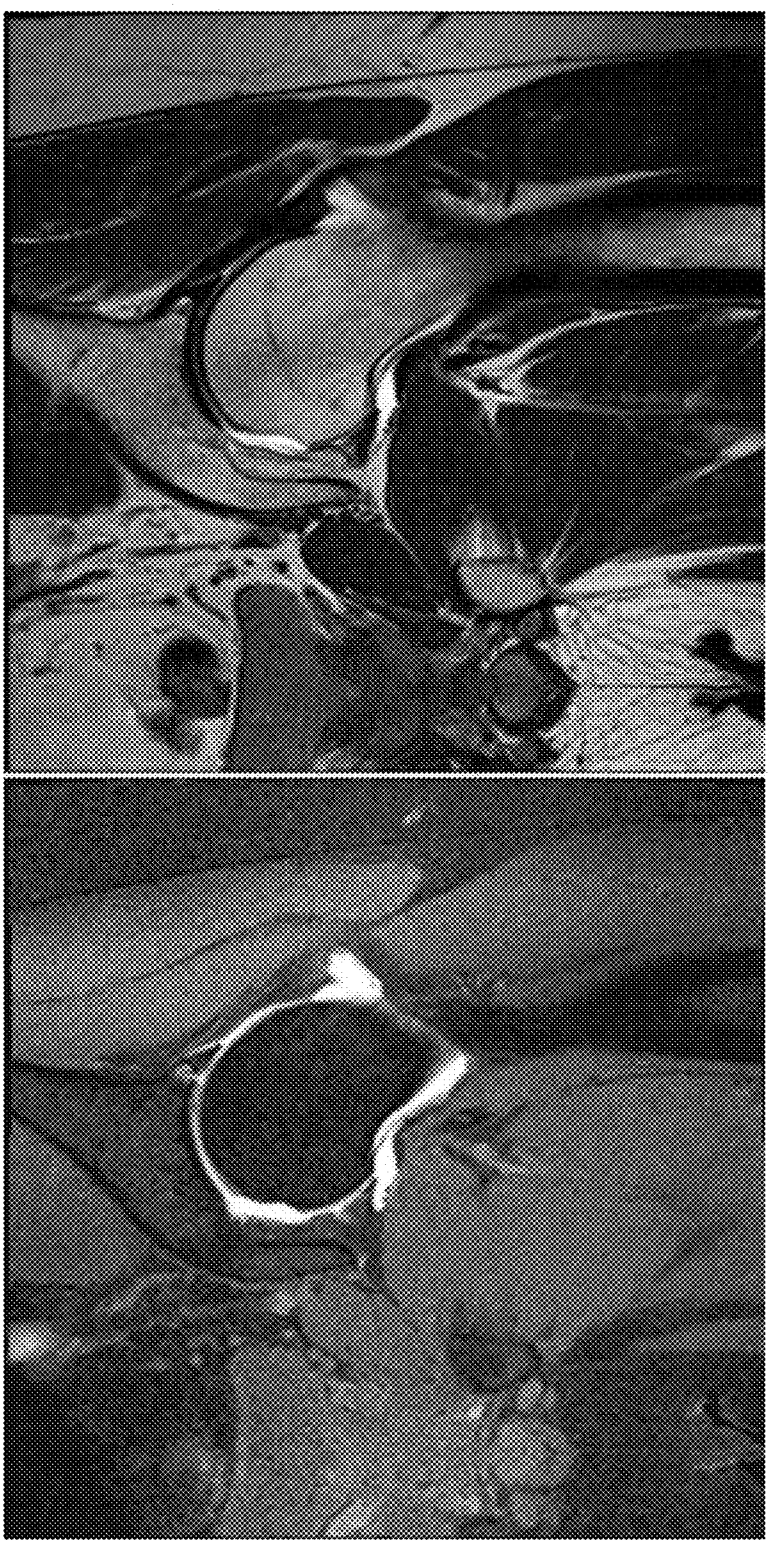
FIG. 5 is a set of coronal fat suppressed T1-weighted TSE images after intraarticular administration of Gadolinium contrast agent on the left and corresponding PD-TSE images on the right. There is clear depiction of chondrolabral separation with associated subchondral cyst formation within the acetabulum best seen on the T1-weighted image.
Figure 6:
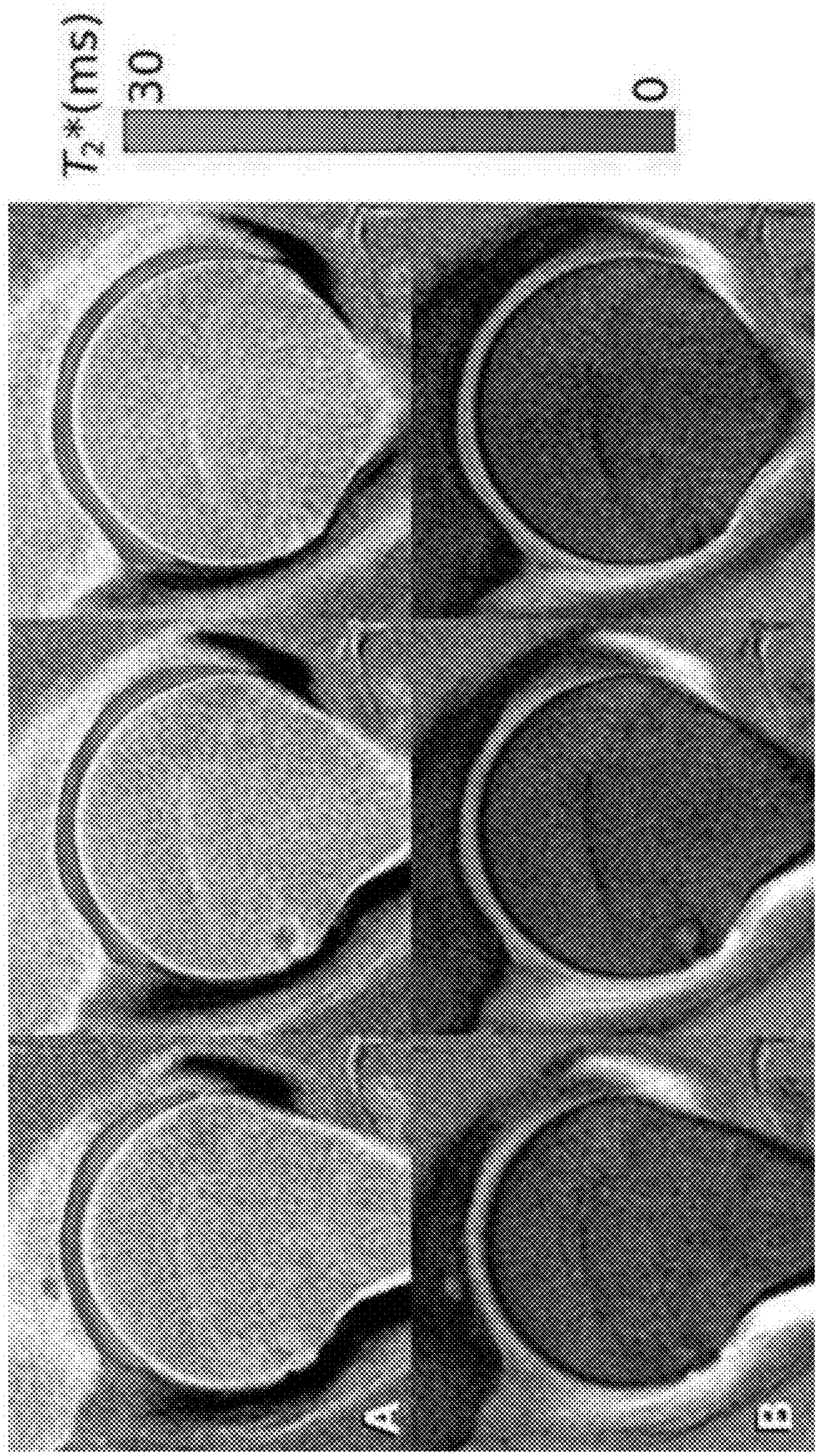
FIG. 6 is a sagittal T2* maps were superimposed on the corresponding three contiguous gradient recalled echo source images with inverted contrast. A gradient recalled T2* images reveal the osseous abnormalities of acetabular subchondral sclerosis and cyst formation as well as the femoral head cyst formation in association with the reduced femoral head neck offset. Please note the exquisite contrast between the acetabulum and the labrum at the echo time of 4 ms. The respective T2* maps of the entire acetabular and femoral head cartilage are shown. Values of acetabular cartilage subjacent to the chondrolabral separation are decreased when compared to normal cartilage. Note preserved cartilage over the central femoral head (values red on color scale=26 ms and above). As found in gold standard arthroscopy, these are areas of preserved cartilage.

Lateral radiographs revealed decreased head-neck offset, an elevated alpha angle of greater than 80 degrees on both cross-table and frog laterals, Tönnis grade 1 joint space preservation, a Tönnis angle of 8 degrees, and lateral center edge angle of 25 degrees. Findings indicated a combined cam and pincer type impingement. MR arthrogram Standard MR arthrographic findings included the presence of a labral tear and question of cartilage involvement along the adjacent acetabular rim. Contrast undermined the anterosuperior labrum at the chondrolabral junction, as illustrated in FIG. 5. A decreased offset of the femoral head-neck junction with associated buttressing was depicted. Sclerosis and subchondral cyst formation was noted (FIG. 6B). The joint space was preserved. T2* maps in the sagittal oblique plane revealed values of 16.4±3.5 ms between the chondrolabral junction and adjacent acetabular cartilage extending from approximately the 3 o'clock to the 12 o'clock position. These values were markedly decreased compared to the 25.9±3.4 ms and 27.5±4.7 ms values for healthy femoral head articular cartilage and healthy acetabular articular cartilage, respectively, as represented in FIG. 6A and detailed in the following table:

TABLE 1

T2* values and arthroscopic scores in the analyzed ROIs. Zones increase from 12 o'clock line towards chondrolabral junction and slices are numbered from lateral to medial. ROIs are indicated on top of the flattened T2* map in FIG. 3.

| | | | Zone | | | | |
|---|---|---|---|---|---|---|---|
| | | | 1 | 2 | 3 | 4 | 5 |
| Pathol-ogy | Slice 1 | T2* (ms) | 10.7<br>4 | 12.1<br>5 | 13.5<br>5 | 15.0<br>5 | 13.8<br>5 |
| | Slice 2 | Arthros-copy | 13.6<br>4 | 19.4<br>5 | 14.2<br>5 | 17.6<br>5 | 19.5<br>5 |
| | Slice 3 | | 17.4<br>4 | 21.8<br>5 | 15.6<br>5 | 20.8<br>4 | 21.0<br>4 |

| | | | 11-11:30 | 10:30-11 |
|---|---|---|---|---|
| Ace-tabular control | Slice 3 | T2* (ms) | 21.6<br>2 | 21.4<br>2 |
| | Slice 4 | Arthros-copy | 31.7<br>2 | 30.3<br>2 |
| | Slice 5 | | 31.0<br>2 | 29.0<br>2 |

As shown in FIG. 7A, the pattern of abnormality, as evidenced by decreased T2* values corresponding to the red color code on the flattened T2* map extended in a narrow band along the chondrolabral junction (pincer lesion). More diffuse areas of severe cartilage abnormalities involving the anterosuperior labrum (cam) and the posterior acetabulum, which has been described as 'contrecoup' lesion associated with cam impingement, were identified.

At the time of arthroscopy, the joint was found to have substantial synovitis, avulsion of the acetabular labrum from 11:30 to 3 o'clock, and cartilage damage of a significant portion of the anterior and superior acetabular cartilage, as illustrated in FIGS. 7B and 7C. The intraoperative assessment of the anterosuperior acetabular cartilage revealed cartilage grades 4 and 5 according to the modified Beck's scale, in the same regions of interest defined for T2* data, as implicated in the immediately-above table. The lateral acetabular rim was denuded of cartilage leaving a cartilage defect with a thin, fibrous base. Areas of carpet phenomenon were identified. More posteriorly, between the 10.30-11.30 o'clock positions an area with relatively normal appearance was noted (acetabular control, grade 2). The superior femoral head at the head-neck junction revealed the point of impingement between the femoral neck and acetabular rim distinguished by an abrupt transition from normal medial femoral head (control area, grade 2) to lateral cartilage destruction. Cam lesion resection resulted in a normal head-neck offset.

There was visual correlation between hip arthroscopy and the flattened T2* map of the acetabulum in the qualitative amount of cartilage damage and its location. The flattened 2-D image of the quantitative 3-D T2* acetabular cartilage map accurately depicted the pattern and degree of cartilage damage found during hip arthroscopy. Likewise, markedly decreased T2* relaxation time values were found in regions of articular cartilage identified as abnormal intraoperatively. The results demonstrate that with T2* relaxation time mapping and 2-D flattening, MR imaging is capable of assessing the quality of articular cartilage in femoroacetabular impingement at a level comparable to the gold standard of diagnostic hip arthroscopy.

MR arthrography and histologic correlations in cadaveric specimens have revealed fibrocartilage transformation with superimposed deposition of calcium hydroxyapatite. Chondroid or fibrocartilaginous metaplasia undergoes mineralization by osteoblasts at the osteochondral junction and subsequent deposition of osteoid matrix. These histological findings were confirmed in symptomatic patients with femoroacetabular impingement. These histological changes, shown to take place with repetitive microtrauma, suggest that the T2* values are likely to be sensitive to changes due to FAI. The results clearly indicate that in areas of cartilage lesions or delamination, T2* values are markedly decreased.

Moreover, the development of a 2-D flattened T2* relaxation time map of the patient's entire acetabular cartilage facilitated more detailed analysis, which demonstrated 1) a pattern of severe focal cartilage damage in a narrow band along the acetabular rim, 2) a large, diffuse area of cartilage abnormality involving the anterosuperior labrum, and 3) a more posterior 'contrecoup' lesion, as would be expected in a mixed type of cam and pincer impingement. The flattened T2* map also accurately correlated with the pattern and degree of cartilage damage found on hip arthroscopy, such as illustrated in FIGS. 7A-7C. Via the 2-D map, information regarding articular cartilage damage is placed, for the first time, in its precise anatomic location facilitating both diagnosis and pre-operative planning. As FAI occurs along an anatomical spectrum of cam, pincer, and mixed cam/pincer lesions with significant management implications based on individual patient anatomy; the diagnostic and prognostic implications of noninvasive tools for mapping the properties of articular cartilage are profound.

The present invention provides systems and method for the use of quantitative T2*-mapping in a patient with femoroacetabular impingement, based on the hypothesis that the degree and pattern of cartilage damage incurred in patients with FAI may be quantified by measuring the properties of articular cartilage with T2* mapping. Furthermore, the present invention demonstrates that this technique can distinguish femoral from acetabular cartilage providing clinically relevant information. Additionally, the present invention describes a novel flattened visualization of the entire acetabular lunate cartilage that affords the unique ability to accurately compare MR to gold standard arthroscopy. By developing a method for flattening the 3-D geometry of the acetabular cartilage for static 2-D visualization of the quantitative T2* maps, pre-operative MR data could be used to correlate intraoperative findings when visualized at the time of arthroscopy.

T2* mapping has, thus, been shown to be uniquely suited to capture the very nature of cartilage damage in femoroacetabular impingement due to its sensitivity to progressive loss of highly organized hyaline cartilage architecture and superimposed microscopic susceptibility changes with calcium deposition, inherent to the disease process. Using this technique, T2* maps were found to have significantly lower values in regions with surgically identified cartilage damage (mean=20.7±6.0 ms) than for normal cartilage (mean=35.3±7.0 ms) in patients with femoroacetabular impingement ($p<0.001$). A receiver operating characteristic (ROC) curve was used to define a threshold T2* value for damaged acetabular cartilage as 28 ms and lower.

Radiographic Tönnis grading is currently the standard of care for excluding patients with moderate cartilage damage (Tönnis grade 2 or greater) for joint preservation surgery. Despite eliminating surgical candidates with joint space narrowing or increased sclerosis, patients with Tönnis grade 1 were found at the time of surgery to have 68 percent (360 of 532) of the regions of interest with cartilage damage and 5 percent (29 of 532) of the regions of interest without any hyaline cartilage. This underscores the insensitivity of radiographs in determining the extent of osteoarthritis in this cohort.

T2* mapping can be a valuable method for routine evaluation of articular cartilage on clinical MR instruments, since it requires little additional time and no intravenous or intraarticular contrast agent is needed. The patient-specific acetabular projection allows for the good anatomic localization of MR data and facilitates both pre-operative patient assessment and the monitoring of specific cartilage lesions over time. The T2* threshold for articular cartilage damage, using the defined protocol at 3T increases the ability to interpret T2* values.

In conclusion, our study indicates that T2* mapping can be a valuable diagnostic method for routine evaluation of acetabular cartilage in FAI on existing clinical MR scanners. The patient-specific acetabular projection allows for good anatomic localization of MRI data, facilitating pre-operative evaluation and long-term cartilage monitoring.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for evaluating tissue states using a magnetic resonance imaging (MRI) system, the method comprising:
- acquiring, with an MRI system, T2* data from a portion of a subject including tissue surrounding a joint;
- generating T2* maps based on the T2* data;
- registering the T2* maps with 3-D anatomical MRI data;
- segmenting the 3-D anatomical MRI data in an ROI;
- generating a 3-D anatomic volume of at least the ROI;
- flattening the 3-D anatomic volume into a 2-D flattened image; and
- presenting the registered T2* maps on the 2-D flattened image.

2. The method of claim 1 further comprising identifying the ROI using anatomical landmarks.

3. The method of claim 2 wherein the landmarks include at least one of an acetabular notch and an acetabular rim.

4. The method of claim 1 further comprising calculating a statistical map by applying a given threshold value indicative of a probability of a disease state.

5. The method of claim 4 wherein the disease state includes diseased cartilage.

6. The method of claim 1 further comprising indicating a threshold T2* value when presenting the registered T2* maps on the 2-D flattened image.

7. The method of claim 6 wherein the threshold T2* value is correlated for damaged articular cartilage.

8. The method of claim 7 wherein the threshold T2* value for damaged acetabular cartilage is 28 ms and lower.

9. The method of claim 1 further comprising acquiring at least one of proton density (PD) and T1-weighted data using at least one of a turbo spin echo (TSE) pulse sequence and a gradient recalled echo (GRE) pulse sequence.

10. A magnetic resonance imaging (MRI) system comprising:
- a magnet system configured to generate a polarizing magnetic field about at least a portion of a subject;
- a plurality of gradient coils configured to apply a gradient field to the polarizing magnetic field;
- a radio frequency (RF) system configured to apply an excitation field to the subject and acquire MR image data therefrom;
- a processor configured to:
  - control the plurality of gradient coils and the RF system to acquire medical imaging data including T2* data from a subject;
  - generate T2* maps based on the T2* data;
  - register the T2* maps with 3-D anatomical data reconstructed from the medical imaging data;
  - segment the 3-D anatomical data in a region of interest (ROI);
  - generate a 3-D anatomic volume of at least the ROI;
  - flatten the 3-D anatomic volume into a 2-D flattened image;
  - a display configured to display the registered T2* maps on the 2-D flattened image.

11. The system of claim 10 further comprising a user interface configured to receive anatomical landmarks to identify the ROI, wherein the anatomical landmarks include at least one of an acetabular notch and an acetabular rim.

12. The system of claim 10 wherein the processor is further configured to correlate the 2-D flattened image and T2* maps with arthroscopy data acquired from at least a portion of tissue of a joint of the subject.

13. The system of claim 10 wherein the processor is configured to apply a threshold T2* value correlated to damage to tissue to at least one of the T2* maps and the 2-D flattened image.

14. The system of claim 13 wherein the processor is further configured to calculate a threshold-based statistical map using the threshold T2* value and the display is configured to display the threshold-based statistical map on the 2-D flattened image.

15. A method of providing medical imaging data comprising:
- acquiring, with an MRI system, medical imaging data including at least T2* data from a subject;
- generating T2* maps based on the T2* data;
- reconstructing 3-D anatomical images of the subject from the medical imaging data;
- registering the T2* maps with the 3-D anatomical images;
- flattening at least one of the 3-D anatomical images into a 2-D flattened image;
- presenting the registered T2* maps on the 2-D flattened image; and
- calculating a statistical map by applying a given threshold value indicative of a probability of a disease state; and
- displaying at least the registered T2* maps or the statistical map on the 2-D flattened image.

16. The method of claim 15 further comprising correlating the registered 2-D flattened image and T2* maps with arthroscopy data acquired from the subject.

17. The method of claim 15 further comprising wherein the given threshold is a time threshold and the disease state includes an affliction to a joint of the subject.

18. The method of claim 15 wherein the registered T2* map is displayed on the 2-D flattened image.

19. The method of claim 15 wherein the statistical map is presented on the 2-D flattened image.

20. The method of claim 15 further comprising indicating a threshold T2* value when displaying the 2-D flattened image and T2* maps correlated to damage to the subject.

21. A non-transitory computer-readable storage medium having stored thereon instructions that, when executed by a computer processor, causes the computer processor to:

acquire medical imaging data including T2* data of a subject;

generate T2* maps based on the T2* data;

register the T2* maps with 3-D anatomical data reconstructed from the medical imaging data;

acquire a 3-D anatomic volume of at least one region of interest (ROI) reconstructed from the 3-D anatomical data;

flatten the 3-D anatomic volume into a 2-D flattened image; and display the registered T2* maps on the 2-D flattened image.

* * * * *

UNITED STATES PATENT AND TRADEMARK OFFICE
CERTIFICATE OF CORRECTION

PATENT NO. : 9,655,562 B2
APPLICATION NO. : 14/088365
DATED : May 23, 2017
INVENTOR(S) : Jutta Ellermann et al.

It is certified that error appears in the above-identified patent and that said Letters Patent is hereby corrected as shown below:

In the Specification

Column 10, Line 47, "con" should be --coil--.

Signed and Sealed this
Twenty-fifth Day of July, 2017

Joseph Matal

Joseph Matal
*Performing the Functions and Duties of the*
*Under Secretary of Commerce for Intellectual Property and*
*Director of the United States Patent and Trademark Office*